United States Patent
Oren

(10) Patent No.: US 11,096,948 B2
(45) Date of Patent: Aug. 24, 2021

(54) **METHODS FOR TREATING *HELICOBACTER* INFECTION**

(71) Applicant: DEXCEL PHARMA TECHNOLOGIES LTD., Or-akiva (IL)

(72) Inventor: Dan Oren, Kfar Shmariahu (IL)

(73) Assignee: DEXCEL PHARMA TECHNOLOGIES LTD., Or-akiva (IL)

( * ) Notice: Subject to any disclaimer, the term of this patent is extended or adjusted under 35 U.S.C. 154(b) by 473 days.

(21) Appl. No.: 16/066,097

(22) PCT Filed: Jan. 16, 2017

(86) PCT No.: PCT/IL2017/050049
§ 371 (c)(1),
(2) Date: Jun. 26, 2018

(87) PCT Pub. No.: WO2017/125912
PCT Pub. Date: Jul. 27, 2017

(65) Prior Publication Data
US 2020/0268769 A1 Aug. 27, 2020

Related U.S. Application Data

(60) Provisional application No. 62/281,270, filed on Jan. 21, 2016.

(51) Int. Cl.
*A61K 31/575* (2006.01)
*A61K 45/06* (2006.01)

(52) U.S. Cl.
CPC ............ *A61K 31/575* (2013.01); *A61K 45/06* (2013.01)

(58) Field of Classification Search
CPC .............................. A61K 31/575; A61K 45/06
See application file for complete search history.

(56) References Cited

U.S. PATENT DOCUMENTS

| | | | |
|---|---|---|---|
| 7,041,313 B1 | 5/2006 | Dietrich et al. | |
| 2004/0170617 A1* | 9/2004 | Finegold | A61K 35/747 424/93.45 |
| 2006/0241040 A1* | 10/2006 | Visintin | C07K 14/705 424/140.1 |
| 2014/0128335 A1* | 5/2014 | Bolla | A61P 31/00 514/29 |

FOREIGN PATENT DOCUMENTS

WO WO 98/22117 * 5/1998

OTHER PUBLICATIONS

Collignon et al., "Fusidic acid in vitro activity", Int. J. Antimicrob. Agents, 1999, 12(2): S45-58 (14 pages).
Sharifi, "Isolation, Analysis and Antimicrobial Activity of the Acidic Fractions of Mastic, Kurdica, Mutica and Cabolica Gums from Genus Pistacia"; Global J. Health Sci., 2012, 4(1): 217-228 (12 pages).
Bebb et al., "Mastic gum has no effect on Helicobacter pylori load in vivo"; J. Antimicrob. Chemotherapy, 2003, 52: 522-523 (2 pages).
Börsch, "Antibiotic Monotherapy"; Helicobacter pylori 1990, Proc. 2nd Inter. Symp. H. pylori, Eds. Heinz Menge et al., Springer Science & Business Media, 210 (1 page).
Chey et al., "American College of Gastroenterology Guideline on the Management of Helicobacter pylori Infection" Am J. Gastroenterol., 2007, 102: 1808-1825 (18 pages).
Jones et al., "American College of Gastroenterology Guideline on the Management of Helicobacter pylori Infection" Can. J. Gastroenterol., 2005, 19(7): 399-408 (11 pages).
Gilchrist et al., "The solid-state characterization of fusidic acid"; Int. J. Pharm., 2012, 422(1-2): 245-53 (9 pages).
Kusters et al., "Pathogenesis of Helicobacter pylori Infection"; Clinical microbial. Rev., 2006, 19(3): 449-490 (42 pages).
Fox et al., "Helicobacter mustelae—Associated Gastritis in Ferrets An Animal Model of Helicobacter pylori Gastritis in Humans"; Gastroenterol., 1990, 99: 352-361 (10 pages).
Dubois et al., "Natural Gastric Infection With Helicobacter pylori in Monkeys: A Model for Spiral Bacteria Infection in Humans"; Gastroenterol., 1994, 106: 1405-1417 (13 pages).
Krakowka et al., "Establishment of Gastric Campylobacter pylori Infection in the Neonatal Gnotobiotic Piglet"; Infec. Immun., 1987, 55(11): 2789-2796 (8 pages).
Radin et al., "Helicobacter pylori Gastric Infection in Gnotobiotic Beagle Dogs"; Infec. Immun., 1990, 58(8): 2606-2612 (7 pages).
Cockerill et al., "Methods for Dilution Antimicrobial Susceptibility Tests for Bacteria That Grow Aerobically; Approved Standard—Ninth Edition"; Clin. Lab. Stand. Inst., 2012, 32(2): M07-A9 (88 pages).
International Search Report for PCT/IL2017/050049, dated Apr. 23, 2017 (3 pages).
Written Opinion of the International Searching Authority for PCT/IL2017/050049, dated Apr. 23, 2017 (7 pages).
Kumar et al., "A Review on Efflux Pump Inhibitors of Gram-Positive and Gram-Negative Bacteria from Plant Sources", International Journal of Current Microbiology and Applied Sciences, Jun. 2016 (20 pages).
Shin et al., "The gastric HK-ATPase: structure, function, and inhibition", Pflugers Arch., Jan. 2009 (28 pages).

* cited by examiner

*Primary Examiner* — Shirley V Gembeh

(74) *Attorney, Agent, or Firm* — Roach, Brown, Mccarthy & Gruber, P.C.; Kevin D. McCarthy

(57) ABSTRACT

Composition and methods suitable for treating *Helicobacter* infection and diseases associated therewith are provided. The composition containing fusidic acid or a pharmaceutically acceptable salt or solvate thereof.

16 Claims, No Drawings

METHODS FOR TREATING *HELICOBACTER* INFECTION

TECHNICAL FIELD

A pharmaceutical composition useful for treating *Helicobacter* infection and diseases associated therewith is provided.

BACKGROUND

*Helicobacter pylori* (*H. pylori*) is a Gram-negative, microaerophilic bacterium which is found in the gastrointestinal tract, mainly in the stomach and the pyloric antrum. It has been associated with the development of peptic ulcers, duodenal ulcers, stomach cancer diseases (including noncardia gastric cancer and Mucosa Associated Lymphoid Tissue (MALT) lymphoma in the stomach), as well as colorectal polyps and colorectal cancer.

Initial therapy as first line treatment of *H. pylori* typically includes a one-week "triple therapy" with a proton pump inhibitor (PPI) and a combination of two antibiotics, clarithromycin and amoxicillin. Variations of the "triple therapy" have been developed mainly in order to overcome penicillin allergy or antibiotic resistance. In penicillin-allergic individuals, metronidazole can be substituted for amoxicillin in equivalent doses. In clarithromycin-resistant individuals, a quadruple therapy was found to be effective. The quadruple therapy typically includes a PPI combined with bismuth subsalicylate and two antibiotics, metronidazole and tetracycline or doxycycline. Variations in quadruple therapy have also been developed, most of which include the use of different combinations of antibiotics.

Duration of treatment which is longer than one week has also been used as well as a sequential therapy involving administration of a PPI and amoxicillin for 5 days, followed by the administration of a PPI and clarithromycin and tinidazole or metronidazole for 5 days. The sequential therapy can be extended to 14 days with administration of a PPI and amoxicillin for 7 days, followed by the administration of a PPI and clarithromycin and tinidazole or metronidazole for 7 days.

Despite successful rates of eradicating *H. pylori* using the hitherto known treatments, an initial first line treatment fails in approximately 20% of patients. This is mainly attributed to antibiotic resistance. Since failed attempts to eradicate *H. pylori* may also elicit secondary antibiotic resistance, it is important to ensure eradication of *H. pylori* at first attempt. Together with the global problem of advancing antimicrobial resistance, there is an unmet need for alternative treatment of *H. pylori* infection.

Fusidic acid is a bacteriostatic antibiotic suitable for the treatment of bacterial infections mainly caused by *Staphylococcus aureus*, *Streptococcus pneumoniae* and *Haemophilus influenzae*. It is a protein synthesis inhibitor that interferes with amino acid transfer from aminoacyl-sRNA to polypeptide on the ribosomes.

Collignon et al. (Int. J. Antimicrob. Agents, 1999, 12(2): S45-58) describe the in vitro activity of fusidic acid. It is shown that while having its principal activity directed at staphylococci, fusidic acid is also active against Gram-positive anaerobic activity, and shows in vitro activity against *Neisseria* spp., *Bordetella pertussis* and *Moraxella catarrhalis*. Collignon et al. further describe that fusidic acid has no activity against other aerobic Gram-negative species and has modest activity against *Streptococcus* and *Enterococcus* spp. as well as Gram-negative anaerobic bacteria.

Sharifi (Global J. Health Sci., 2012, 4(1): 2017-228) describes the isolation and characterization of the chemical entities of mastic, kurdica, mutica and cabolica gums from genus Pistacia. These chemical entities were screened for anti-microbial activities against nine strains of *H. pylori* and some other Gram-negative and Gram-positive bacteria. The most bioactive components were structurally analyzed. These components mimic steroid compounds, in particular, the known antibiotic fusidic acid.

Bebb et al. (J. Antimicrob. Chemotherapy, 2003, 52: 522-523) tested mastic gum ability to suppress or eradicate *H. pylori* infection in humans. Nine patients with *H. pylori* infection, and without gastroduodenal ulceration, were recruited from day-case endoscopy lists and treated with 1 g mastic four times daily for 14 days. [$^{13}$C] Urea Breath Tests (UBTs) were carried out immediately before, on day 15, and 5 weeks after treatment with mastic. Mastic had no effect on *H. pylori* status in any of the eight completed patients; all remained *H. pylori* positive by UBT with no change in 6 scores. Bebb et al. concludes that despite reported anti-*H. pylori* action in vitro, the preliminary study shows that mastic has no effect on *H. pylori* in humans.

The activity of fusidic acid against *H. pylori* infection has been tested. Börsch describes that fusidic acid has proven to be ineffective as monotherapy against *H. pylori* (*Helicobacter pylori* 1990: Proc. 2$^{nd}$ Inter. Symp. *H. pylori*, Eds. Menge et al., 1989: 2010).

There is an unmet need for an effective treatment of *Helicobacter* infection that results in higher eradication rates of the infection.

SUMMARY

Provided herein are compositions and methods for treating and preferably eradicating *Helicobacter* infection and diseases associated therewith including peptic ulcers, duodenal ulcers, stomach cancer diseases (including noncardia gastric cancer and MALT lymphoma in the stomach), as well as colorectal polyps and colorectal cancer.

Unexpectedly, it has now been found that fusidic acid and sodium fusidate are effective in treating *H. pylori* infection and related diseases, either alone or in combination with conventional therapy modes.

In one embodiment, there is provided a method for treating *Helicobacter* infection in a subject in need thereof, the method comprising the step of administering to the subject a pharmaceutical composition comprising a therapeutically effective amount of fusidic acid or a pharmaceutically acceptable salt or solvate thereof.

In another embodiment, there is provided a method for suppressing *Helicobacter* replication, the method comprising the step of administering to a subject in need thereof a pharmaceutical composition comprising a therapeutically effective amount of fusidic acid or a pharmaceutically acceptable salt or solvate thereof.

In some embodiments, there is provided a pharmaceutical composition comprising a therapeutically effective amount of fusidic acid or a pharmaceutically acceptable salt or solvate thereof, for use in treating *Helicobacter* infection.

In other embodiments, there is provided a pharmaceutical composition comprising a therapeutically effective amount of fusidic acid or a pharmaceutically acceptable salt or solvate thereof, for use in suppressing *Helicobacter* replication.

In one embodiment, the *Helicobacter* species is *H. pylori*. In another embodiment, treating comprises eradication of *H. pylori* bacteria.

In specific embodiments, the *H. pylori* bacteria comprise a strain resistant to antibiotics known as useful in treating *H. pylori* infection. In exemplary embodiments, the *H. pylori* bacteria comprise a strain resistant to macrolides. In other exemplary embodiments, the *H. pylori* bacteria comprise a strain resistant to clarithromycin. In yet another exemplary embodiment, the *H. pylori* bacteria comprise a strain resistant to rifabutin or rifamycin. Each possibility represents a separate embodiment.

In yet other embodiments, there is provided a method of treating a gastric or duodenal ulcer associated with *Helicobacter* infection comprising the step of administering to a subject in need thereof a pharmaceutical composition comprising fusidic acid or a pharmaceutically acceptable salt or solvate thereof.

In various embodiments, there is provided a composition comprising fusidic acid or a pharmaceutically acceptable salt or solvate thereof for use in treating a gastric or duodenal ulcer associated with *Helicobacter* infection.

In further embodiments, there is provided a method of treating *Helicobacter* infection having oncomodulatory activity associated with the development of a stomach cancer disease, colorectal polyps or colorectal cancer, the method comprising the step of administering to a subject in need thereof a pharmaceutical composition comprising fusidic acid or a pharmaceutically acceptable salt or solvate thereof.

In additional embodiments, provided herein is a pharmaceutical composition comprising a therapeutically effective amount of fusidic acid or a pharmaceutically acceptable salt or solvate thereof, for use in treating *Helicobacter* infection having oncomodulatory activity associated with the development of a stomach cancer disease, colorectal polyps or colorectal cancer. Each possibility represents a separate embodiment.

In particular embodiments, the stomach cancer disease is selected from noncardia gastric cancer and MALT lymphoma in the stomach with each possibility representing a separate embodiment.

In certain embodiments, the fusidic acid or a pharmaceutically acceptable salt or solvate thereof have a minimum inhibitory concentration (MIC) of about 10 µg/ml or less against *Helicobacter*.

In other embodiments, the fusidic acid or a pharmaceutically acceptable salt or solvate thereof is administered at a daily dose of about 0.001 to about 1,000 mg/kg body weight.

In one embodiment, the pharmaceutical composition disclosed herein further comprises a pharmaceutically acceptable carrier or excipient.

In various embodiments, the pharmaceutical composition is suitable for oral administration.

According to some embodiments, the pharmaceutical composition is in the form selected from the group consisting of tablet, pill, capsule, pellets, granules, powder, lozenge, sachet, cachet, elixir, suspension, dispersion, emulsion, solution, syrup, aerosol, ointment, and suppository, with each possibility representing a separate embodiment of the disclosure.

In additional embodiments, the fusidic acid or a pharmaceutically acceptable salt or solvate thereof is co-administered in combination with at least one other drug. The at least one other drug may be a proton pump inhibitor, a $H_2$ receptor antagonist, an antacid, an antibiotic other than fusidic acid or a pharmaceutically acceptable salt or solvate thereof, or a combination thereof. Each possibility represents a separate embodiment.

Certain embodiments include the co-administration of the fusidic acid or a pharmaceutically acceptable salt or solvate thereof with an antibiotic including, but not limited to, antibiotic detailed in American College of Gastroenterology Guideline on the Management of *Helicobacter* pylori Infection and antibiotic detailed in the Canadian *Helicobacter* Study Group. Non-limiting antibiotics suitable for co-administration with the fusidic acid or a pharmaceutically acceptable salt or solvate thereof are selected from metronidazole, clarithromycin, amoxicillin, tetracycline, doxycycline, levofloxacin, rifabutin, rifamycin and mixtures thereof with each possibility representing a separate embodiment. In some embodiments, the proton pump inhibitor comprises at least one of omeprazole, lansoprazole, pantoprazole, rabeprazole, tenatoprazole and pharmaceutically acceptable salts thereof including solvates, isomers, isomorphs, polymorphs, pseudopolymorphs, and prodrugs thereof. In other embodiments, there is provided the co-administration of fusidic acid or a pharmaceutically acceptable salt or solvate thereof with a $H_2$ receptor antagonist. In particular embodiments, the $H_2$ receptor antagonist comprises at least one of cimetidine, ranitidine, famotidine, roxatidine, nizatidine, and lafutidine with each possibility representing a separate embodiment. Various embodiments include the co-administration of the fusidic acid or a pharmaceutically acceptable salt or solvate thereof with an antacid. Exemplary antacids include, but are not limited to, hydroxides such as aluminum hydroxide and magnesium hydroxide, bicarbonates such as sodium bicarbonate and potassium bicarbonate, carbonates such as magnesium carbonate and calcium carbonate, silicates such as aluminum silicate and magnesium silicate, aminoacetic acid, magnesium metasilicic aluminate, magnesium oxide, and bismuth-containing compounds such as bismuth citrate, bismuth subcitrate, bismuth salicylate, bismuth subsalicylate, bismuth tartrate, bismuth sodium tartrate, bismuth nitrate, bismuth gallate, and bismuth subgallate with each possibility representing a separate embodiment.

In particular embodiments, the fusidic acid or a pharmaceutically acceptable salt or solvate thereof and the at least one other drug together provide a therapeutic anti-bacterial effect against *Helicobacter* which is at least additive.

In further embodiments, co-administration of the fusidic acid or a pharmaceutically acceptable salt or solvate thereof and the at least one other drug is performed in a regimen selected from a single combined composition, separate individual compositions administered substantially at the same time, and separate individual compositions administered under separate schedules. Each possibility represents a separate embodiment of the disclosure.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION

There is provided a pharmaceutical composition for use in treating, preventing, attenuating, and/or inhibiting *Helicobacter* infection, particularly *H. pylori* infection. The pharmaceutical composition comprises fusidic acid or a pharmaceutically acceptable salt or solvate thereof. The pharmaceutical composition is also useful in treating various diseases and disorders associated with *Helicobacter* infection including, but not limited to, peptic ulcers (duodenal and gastric) and stomach cancer diseases such as noncardia gastric cancer and MALT lymphoma in the stomach as well as colorectal polyps and colorectal cancer.

The present disclosure is based in part on the unexpected finding of bacteriostatic and/or bacteriocidic action of fusidic acid or a pharmaceutically acceptable salt or solvate thereof (e.g. sodium fusidate) against *H. pylori*. Surprisingly, in vitro studies show that fusidic acid and sodium fusidate are active against different strains of *H. pylori*. This finding provides a significant advantage over the hitherto known treatments, by increasing the percentage of patients in which eradication is achieved, reducing doses and side effects of conventional add-on therapy, preserving gut microbiota, and decreasing exposure to conventional antibiotics thereby decreasing antibiotic resistance. In addition, fusidic acid and/or salts and solvates thereof have no cross-resistance with the existing antibiotics used for the treatment of *H. pylori* and have low probability for developing resistance.

Disclosed herein is a method of treating, preventing, attenuating, and inhibiting *Helicobacter* replication, infection and diseases associated with *Helicobacter* infection comprising administering to a subject in need thereof a pharmaceutical composition comprising fusidic acid or a pharmaceutically acceptable salt or solvate thereof. Further disclosed is the use of fusidic acid or a pharmaceutically acceptable salt or solvate thereof in the preparation of a medicament for treating, preventing, attenuating, and inhibiting *Helicobacter* replication, infection and diseases associated with *Helicobacter* infection.

The term "treating" as used herein includes the diminishment, alleviation, or amelioration of at least one symptom associated or caused by the state, disorder or disease being treated. In some embodiments, the term "treating" as used herein refers to the inhibition of *Helicobacter* replication with reduction of bacterial load. In other embodiments, the term "treating" encompasses essentially complete eradication of the *Helicobacter* species. It is contemplated that the term "treating" as used herein refers to a first line treatment as well as to second or third lines of therapy with each possibility representing a separate embodiment of the disclosure.

It will be understood by those skilled in the art that the compositions and methods disclosed herein have utility for treating not only *Helicobacter* infection, but also diseases and disorders engendered by the *Helicobacter* infection. Thus, for example, there is provided a composition and method of treating peptic ulcers (duodenal and gastric), colorectal polyps, colorectal cancer, and stomach cancer diseases including, but not limited to, noncardia gastric cancer and MALT lymphoma in the stomach comprising administering to a subject in need thereof a therapeutically effective amount of fusidic acid or a pharmaceutically acceptable salt or solvate thereof. The composition and method disclosed herein encompass the direct targeting of *Helicobacter* in subjects having peptic ulcers (duodenal and gastric), colorectal polyps, colorectal cancer, and stomach cancer diseases and/or targeting the peptic ulcers (duodenal and gastric) and modulating the transformed phenotype of colorectal polyps, colorectal cancer, and stomach cancer diseases. In some embodiments, the composition and method disclosed herein prevent or decrease the likelihood of developing peptic ulcers (duodenal and gastric), colorectal polyps, colorectal cancer, and stomach cancer diseases in subjects who are afflicted with *Helicobacter*. In other embodiments, provided herein is a composition and method of treating a gastric ulcer comprising administering to a subject in need thereof a therapeutically effective amount of fusidic acid or a pharmaceutically acceptable salt or solvate thereof. In further embodiments, provided herein is a composition and method of treating atrophic gastritis comprising administering to a subject in need thereof a therapeutically effective amount of fusidic acid or a pharmaceutically acceptable salt or solvate thereof.

The term "a therapeutically effective amount" as used herein refers to an amount of an agent which is effective, upon single or multiple dose administration to the subject in providing a therapeutic benefit to the subject. In one embodiment, the therapeutic benefit is inhibiting *Helicobacter* activity. As used herein, the term "administering" refers to bringing in contact with the compound or composition disclosed herein. Administration can be accomplished to cells or tissue cultures, or to living organisms, for example mammals, in particular humans.

Fusidic acid is chemically known as 29-Nordammara-17 (20),24-dien-21-oic acid, 16-(acetyloxy)-3,11-dihydroxy-, (3α, 4α, 8α, 9α, 11α, 13α, 14β, 16β, 17Z)- and is represented by the following structure:

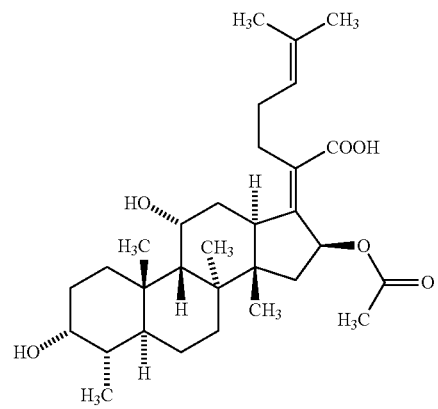

Fusidic acid can be isolated from the fermentation broth of *Fusidium coccineum*. Alternatively, it can be synthesized using methods known to those of skill in the art of chemical synthesis.

Pharmaceutically acceptable salts of fusidic acid as used herein refer to any salt that is pharmaceutically acceptable and has the desired pharmacological properties. Such salts, typically formed by the carboxylic acid group present in fusidic acid include those that may be derived from an inorganic or organic base, including amino acids, which is non-toxic and/or bio-acceptable.

Suitable pharmaceutically acceptable base addition salts include, but are not limited to, metallic salts of sodium, calcium, lithium, magnesium, potassium, strontium, aluminum and zinc; ammonium salts derived from ammonia, primary, secondary, tertiary and quaternary amines, non-limiting examples of which are trimethylamine, cyclohexylamine, benzylamine, dibenzylamine, 2-hydroxyethylamine, bis(2-hydroxyethyl)amine, phenyl ethylbenzyl amine, dibenzylethylenediamine, procaine, chloroprocaine, quinine, choline, and N-methylglucosamine. Salts with amino acids such as glycine, ornithine, histidine, phenylglycine, lysine, and arginine are contemplated. Furthermore, any zwitterionic form of the fusidic acid formed by a carboxylic acid and an amino group are contemplated as well. According to the principles disclosed herein, the pharmaceutically acceptable salt may be formed by known methods in which the free acid form is brought into contact with a sufficient amount of the desired base to produce the salt which may be subsequently isolated as is known in the art.

In one embodiment, the pharmaceutically acceptable salt of fusidic acid is sodium fusidate.

Pharmaceutically acceptable salts of fusidic acid may also comprise a counterion which contains one or more chiral centers so that different diastereomeric pairs or mixtures of such diastereomeric pairs of these salts are possible. It is to be understood that the term "fusidic acid" relates to all the individual enantiomers, diastereomers and respective racemic and non-racemic mixtures thereof. These mixtures of enantiomers and diastereomers can be separated into stereoisomerically uniform components in a known manner or synthesized a priori as separate enantiomers and diastereomers.

In certain embodiments, the pharmaceutical composition may include solvates of fusidic acid or salts thereof. The term "solvate" as used herein refers to a physical association of fusidic acid or salts thereof with one or more solvent molecules. This physical association involves varying degrees of ionic and covalent bonding, including hydrogen bonding. "Solvate" encompasses both solution-phase and isolatable solvates. Non-limiting examples of suitable solvates include ethanolates, methanolates and the like. A "hydrate" is a solvate wherein the solvent molecule is water.

As used herein, fusidic acid may also include polymorphs of fusidic acid or salts and solvates thereof. The term "polymorph" refers to a particular crystalline or amorphous state of a substance, which can be characterized by particular physical properties such as X-ray diffraction, electron diffraction, IR spectra, Raman spectra melting point, and the like. Suitable forms of fusidic acid or salts and solvates thereof include, but are not limited to, forms I, II, III, and IV as described by Gilchrist et al. in Int. J. Pharm., 2012, 422(1-2): 245-53 with each possibility representing a separate embodiment.

In further embodiments, the fusidic acid or a pharmaceutically acceptable salt or solvate thereof have a minimum inhibitory concentration (MIC) of about 10 µg/ml or less against *Helicobacter*. According to certain embodiments, the fusidic acid or a pharmaceutically acceptable salt or solvate thereof has MIC within the range of about 0.0001 to about 10 µg/ml against *Helicobacter*. For example, the fusidic acid or a pharmaceutically acceptable salt or solvate thereof has MIC within the range of about 0.0001 to about 0.5 µg/ml, about 0.001 to about 0.5 µg/ml, about 0.01 to about 0.5 µg/ml, about 0.5 to about 1 µg/ml, about 0.5 to about 8 µg/ml, about 1 to about 6 µg/ml, or about 2 to about 5 µg/ml, with each possibility representing a separate embodiment. Methods for determination of MIC include, but are not limited to, agar dilution method, broth micro dilution method, epsilometer method, turbidimetric method, and disk diffusion method. Each possibility represents a separate embodiment of the disclosure.

Typically, fusidic acid or a pharmaceutically acceptable salt or solvate thereof is administered as a pharmaceutical composition together with a pharmaceutically acceptable excipient. A pharmaceutically acceptable excipient may be any material with which the active ingredient is formulated to facilitate administration. The pharmaceutical composition disclosed herein may contain from about 0.5% to about 95% by weight of active ingredient. In further embodiments, the pharmaceutical composition disclosed herein may contain from about 0.01% to about 0.5% by weight of active ingredient.

Pharmaceutical compositions may be in the form of tablets, pills, capsules (such as soft or hard gelatin capsules), pellets, granules, powders (such as sterile packaged powders), lozenges, sachets, cachets, elixirs, suspensions, dispersions, emulsions, solutions (such as sterile injectable solutions), syrups, aerosols, ointments, and suppositories with each possibility representing a separate embodiment. These compositions can be produced by known methods using conventional solid or liquid excipient(s).

Suitable excipients include, but are not limited to, a binder, a filler, a surfactant, an anti-tacking agent, a plasticizer, a lubricant, a glidant, a disintegrant, a diluent, a tonicity enhancing agent, a wetting agent, a buffering substance, a colorant, a preservative, and any combination thereof, with each possibility representing a separate embodiment.

Suitable binders within the scope of the present disclosure include, but are not limited to, polyvinylpyrrolidone, copovidone, hydroxypropylmethyl cellulose, hydroxypropyl cellulose, starch, gelatin, or sugars. Sugars include sucrose, dextrose, molasses, and lactose, with each possibility representing a separate embodiment.

Suitable fillers within the scope of the present disclosure include, but are not limited to, sugars such as lactose, sucrose, mannitol or sorbitol and derivatives therefore (e.g. amino sugars), ethylcellulose, microcrystalline cellulose, silicified microcrystalline cellulose and the like, with each possibility representing a separate embodiment.

Suitable surfactants within the scope of the present disclosure include, but are not limited to, non-ionic, anionic or cationic surfactants. Typically, surfactants may have one lipophilic and one hydrophilic group in the molecule. The surfactant may optionally comprise one or more of soaps, detergents, emulsifiers, dispersing and wetting agents. More specifically, surfactants may optionally comprise, for example, one or more of polysorbate, stearyltriethanolamine, sodium lauryl sulfate, sodium taurocholate, laurylaminopropionic acid, lecithin, benzalkonium chloride, benzethonium chloride and glycerin monostearate; and hydrophilic polymers such as polyvinyl alcohol, polyvinylpyrrolidone, carboxymethylcellulose sodium, methylcellulose, hydroxymethylcellulose, hydroxyethylcellulose and hydroxypropylcellulose among others, with each possibility representing a separate embodiment.

Suitable anti-tacking agents within the scope of the present disclosure include, but are not limited to, magnesium stearate, calcium stearate, stearic acid, talc, mica, colloidal silicon and the like among others, with each possibility representing a separate embodiment.

Suitable plasticizers within the scope of the present disclosure include, but are not limited to, cetyl alcohol, dibutyl sebacate, polyethylene glycol, polypropylene glycol, dibutyl phthalate, diethyl phthalate, triethyl citrate, tributyl citrate, acetylated monoglyceride, acetyl tributyl citrate, triacetin, dimethyl phthalate, benzyl benzoate, butyl and/or glycol esters of fatty acids, refined mineral oils, oleic acid, castor oil, corn oil, camphor, glycerol and sorbitol among others, with each possibility representing a separate embodiment.

Suitable lubricants within the scope of the present disclosure include, but are not limited to, sodium stearyl fumarate, stearic acid, polyethylene glycol, or stearates, such as magnesium stearate, with each possibility representing a separate embodiment.

A suitable glidant within the scope of the present disclosure is e.g., colloidal silicon dioxide.

Suitable disintegrants within the scope of the present disclosure include, but are not limited to, crospovidone, croscarmelose sodium, a sugar alcohol, a cellulose derivative, cross-linked derivatives of starch (e.g. sodium starch glycolate), pregelatinized starch, crosslinked sodium carboxymethyl cellulose, low substituted hydroxypropylcellulose and any combination or mixture thereof, with each possibility representing a separate embodiment. Additional disintegrants include, but are not limited to, silicates, carbonates, polyoxyethylene sorbitan fatty acid esters, stearic monoglyceride, guar gum, and lactose. Suitable sugar alcohols include, but are not limited to, mannitol, sorbitol, maltitol, xylitol, and any combination or mixtures thereof. Additional sugar alcohols include, but are not limited to, arabitol, isomalt, erythritol, glycerol, lactitol, and mixtures thereof. Suitable cellulose derivatives include, but are not limited to, methylcellulose, cross-linked carboxylic methylcelluloses, microcrystalline cellulose and any combination or mixture thereof. Each possibility represents a separate embodiment.

Suitable diluents include, but are not limited to, dicalcium phosphate dihydrate, sugars, lactose, calcium phosphate, cellulose, kaolin, mannitol, sodium chloride, and dry starch, with each possibility representing a separate embodiment.

Suitable tonicity enhancing agents include, but are not limited to, ionic and non-ionic agents. For example, ionic compounds include, but are not limited to, alkali metal or alkaline earth metal halides, such as, for example, $CaCl_2$ KBr, KCl, LiCl, NaI, NaBr, and NaCl. Non-ionic tonicity enhancing agents are, for example, urea, glycerol, sorbitol, mannitol, propylene glycol, and dextrose, with each possibility representing a separate embodiment.

Suitable wetting agents include, but are not limited to, glycerin, starches, and the like. Each possibility represents a separate embodiment.

Suitable buffering substances include, but are not limited to, acidic buffering agents such as short chain fatty acids, citric acid, acetic acid, hydrochloric acid, sulfuric acid, and fumaric acid; and basic buffering agents such as tris, sodium carbonate, sodium bicarbonate, sodium hydroxide, potassium hydroxide, and magnesium hydroxide, with each possibility representing a separate embodiment.

Suitable colorants include, but are not limited to, alumina (dried aluminum hydroxide), annatto extract, calcium carbonate, canthaxanthin, caramel, β-carotene, cochineal extract, carmine, potassium sodium copper chlorophyllin (chlorophyllin-copper complex), dihydroxyacetone, bismuth oxychloride, synthetic iron oxide, ferric ammonium ferrocyanide, ferric ferrocyanide, chromium hydroxide green, chromium oxide greens, guanine, mica-based pearlescent pigments, pyrophyllite, mica, dentifrices, talc, titanium dioxide, aluminum powder, bronze powder, copper powder, and zinc oxide, with each possibility representing a separate embodiment.

Suitable preservatives include, but are not limited to, quaternary ammonium salts such as benzalkonium chloride, benzoxonium chloride or polymeric quaternary ammonium salts, alkyl-mercury salts of thiosalicylic acid, such as, for example, thiomersal, phenylmercuric nitrate, phenylmercuric acetate or phenylmercuric borate, parabens, such as, for example, methylparaben or propylparaben, alcohols, such as, for example, chlorobutanol, benzyl alcohol or phenyl ethanol, guanidine derivatives, such as, for example, chlorohexidine or polyhexamethylene biguanide, sorbic acid or ascorbic acid, with each possibility representing a separate embodiment.

Additional excipients that may be incorporated in the compositions disclosed herein include agents that aid mucosal adhesion and facilitate local treatment such as, but not limited to, hydroxypropyl cellulose, hydroxypropyl methyl cellulose, sodium carboxymethyl cellulose, maleic anhydride copolymer (e.g., Gantrez), and agents that control release such as polyacrylic copolymer (e.g. Carbopol 934). Each possibility represents a separate embodiment.

Suitable routes of administration of the compositions disclosed herein include, for example, oral, rectal, transdermal, topical, transmucosal, transnasal, intestinal or parenteral delivery, including intramuscular, subcutaneous and intramedullary injections as well as intrathecal, direct intraventricular, intravenous, inrtaperitoneal, intranasal including via a nasogastric tube, intraarterial, intravesicle (into the bladder) or intraocular injections with each possibility representing a separate embodiment. According to certain embodiments, the compositions are particularly suitable for oral administration. It is contemplated that by orally administering the compositions, a systemic effect as well as a local effect can be achieved. In one embodiment, the compositions are administered through the nasal respiratory route. Compositions in pharmaceutically acceptable solvents may be nebulized by use of inert gases. Nebulized solutions may be breathed directly from the nebulizing device or the nebulizing device may be attached to a face mask tent, or intermittent positive pressure breathing machine. Solution, suspension, or powder compositions may be administered, orally or nasally, from devices that deliver the composition in an appropriate manner.

The administration regimen can be determined by a skilled artisan depending on the infection and the severity of the condition, the patient population, age, weight etc. The amount of fusidic acid or a pharmaceutically acceptable salt or solvate thereof that will be effective in the treatment depends on the nature of the disorder or condition to be treated, and can be determined by standard clinical techniques. In addition, in vitro assays, in vivo assays and ex-vivo assays may optionally be employed to help identify optimal dose ranges. The precise dose to be employed also depends on the route of administration, and the progression of the disease or disorder, and should be decided according to the judgment of the practitioner and each patient's circumstances. Typically, doses in the range of 0.001-1000 mg/kg of body weight, 0.01 mg/kg to 100 mg/kg, 0.1 mg/kg to 100 mg/kg, 1 mg/kg to 100 mg/kg, 10 mg/kg to 75 mg/kg, etc. may be used. Exemplary, non-limiting amounts include 0.5 mg/kg, 1 mg/kg, 5 mg/kg, 10 mg/kg, 20 mg/kg, 50 mg/kg, 60 mg/kg, 75 mg/kg and 100 mg/kg with each possibility representing a separate embodiment. Effective doses may be extrapolated from dose-response curves derived from in vitro, animal model or ex-vivo model test bioassays or systems. Typical fixed doses include, but not limited to, 5 mg, 10 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1,000 mg with each possibility representing a separate embodiment.

The administration schedule can be taken once-daily, twice-daily, thrice-daily, once-weekly, twice-weekly, thrice-weekly, once-monthly, twice-monthly, thrice-monthly, or any other administration schedule known to those of skill in the art. Provided herein are pharmaceutical compositions that exhibit release profiles that comprise any/all possible modes of release profiles including, but not limited to, immediate release (IR), or modified release such as delayed release (DR), sustained release (SR) and extended release (XR) formulations. Each possibility represents a separate embodiment.

In addition, the administration can be continuous, i.e., every day, or intermittent. The terms "intermittent" or "intermittently" as used herein refer to stopping and starting at either regular or irregular intervals. For example, intermittent administration can be administration in one to six days per week or it may mean administration in cycles (e.g. daily administration for two to eight consecutive weeks, then a rest period with no administration for up to one week) or it may mean administration on alternate days.

In one embodiment, the compositions and methods disclosed herein are directed at the treatment of H. pylori infection and diseases associated therewith. According to some embodiments, fusidic acid or a pharmaceutically acceptable salt or solvate thereof is used as a monotherapy. The use of fusidic acid or a pharmaceutically acceptable salt or solvate thereof is particularly advantageous when the H. pylori bacteria comprise a strain resistant to conventional antibiotics. In specific embodiments, the pylori bacteria comprise a strain resistant to macrolides. In additional embodiments, the H. pylori bacteria comprise a strain resistant to clarithromycin. In further embodiments, the H. pylori bacteria comprise a strain resistant to rifabutin or rifamycin. Each possibility represents a separate embodiment.

In certain embodiments, the composition comprising fusidic acid or a pharmaceutically acceptable salt or solvate thereof as disclosed herein is active against a single H. pylori strain. In other embodiments, the composition comprising fusidic acid or a pharmaceutically acceptable salt or solvate thereof as disclosed herein is active against a plurality of H. pylori strains. Non-limiting examples of H. pylori strains against which the compositions disclosed herein are active include, but are not limited to, 26695, J99, RSB6, P10, SS1, SS2000, N6, NCTC 11637, RU1, 86-313, HPAG1, Shi470, G27, Tx30a, ATCC 43504 and combinations thereof with each possibility representing a separate embodiment. Additional examples of H. pylori ATCC strains against which the compositions disclosed herein are active include, but are not limited to, 700824, 700392, 43504, 43579, 51653, 43826 and combinations thereof with each possibility representing a separate embodiment. In further embodiments, the composition comprising fusidic acid or a pharmaceutically acceptable salt or solvate thereof as disclosed herein is active against H. pylori positive for cytotoxin-associated gene A (CagA). In yet other embodiments, the composition comprising fusidic acid or a pharmaceutically acceptable salt or solvate thereof as disclosed herein is active against H. pylori positive for vacuolating cytotoxin A (VacA).

According to additional embodiments, there is provided a combination therapy comprising fusidic acid or a pharmaceutically acceptable salt or solvate thereof and at least one other drug.

In one embodiment, fusidic acid or a pharmaceutically acceptable salt or solvate thereof is used in combination with a proton pump inhibitor. In another embodiment, the proton pump inhibitor is selected from the group consisting of omeprazole, lansoprazole, pantoprazole, rabeprazole, tenatoprazole and pharmaceutically acceptable salts thereof, with each possibility representing a separate embodiment. It is contemplated that any solvates, isomers, isomorphs, polymorphs, pseudopolymorphs, and prodrugs of the aforementioned proton pump inhibitors are within the scope of the combination therapy with fusidic acid or a pharmaceutically acceptable salt or solvate thereof.

In certain embodiments, fusidic acid or a pharmaceutically acceptable salt or solvate thereof is used in combination with an antibiotic other than fusidic acid or a pharmaceutically acceptable salt or solvate thereof. In specific embodiments, the antibiotic includes, but is not limited to, metronidazole, clarithromycin, amoxicillin, tetracycline, doxycycline, levofloxacin, rifabutin, rifamycin, and any other antibiotic known in the art to be effective in treating Helicobacter infection including any combination of the aforementioned antibiotics. Each possibility represents a separate embodiment.

In various embodiments, fusidic acid or a pharmaceutically acceptable salt or solvate thereof is used in combination with a H, receptor antagonist. In several embodiments, the H, receptor antagonist includes, but is not limited to, cimetidine, is ranitidine, famotidine, roxatidine, nizatidine, and lafutidine with each possibility representing a separate embodiment.

Additional embodiments include the combination therapy of fusidic acid or a pharmaceutically acceptable salt or solvate thereof with an antacid. In some embodiments, the antacid includes, but is not limited to, hydroxides such as aluminum hydroxide and magnesium hydroxide, bicarbonates such as sodium bicarbonate and potassium bicarbonate, carbonates such as magnesium carbonate and calcium carbonate, silicates such as aluminum silicate and magnesium silicate, aminoacetic acid, magnesium metasilicic aluminate, magnesium oxide, and bismuth-containing compounds such as bismuth citrate, bismuth subcitrate, bismuth salicylate, bismuth subsalicylate, bismuth tartrate, bismuth sodium tartrate, bismuth nitrate, bismuth gallate, and bismuth subgallate, with each possibility representing a separate embodiment.

In one embodiment, fusidic acid or a pharmaceutically acceptable salt or solvate thereof is used in combination with at least two other drugs. In some embodiments, the at least two other drugs comprise a proton pump inhibitor and an antibiotic other than fusidic acid or a pharmaceutically acceptable salt or solvate thereof. In other embodiments, the fusidic acid or a pharmaceutically acceptable salt or solvate thereof is used in combination with a proton pump inhibitor, an antacid and an antibiotic other than fusidic acid or a pharmaceutically acceptable salt or solvate thereof.

Should the compositions disclosed herein be administered as a combination therapy with additional therapeutic agent(s), the treatment may take place sequentially in any order, simultaneously or a combination thereof. For example, administration of fusidic acid or a pharmaceutically acceptable salt or solvate thereof can take place prior to, after or at the same time as the administration of the additional therapeutic agent(s). For example, a total treatment period can be decided for the fusidic acid or a pharmaceutically acceptable salt or solvate thereof. The additional agent(s) can be administered prior to the onset of treatment with the fusidic acid or a pharmaceutically acceptable salt or solvate thereof or following treatment with the fusidic acid or a pharmaceutically acceptable salt or solvate thereof. In addition, the additional agent(s) can be administered during the period of administering the fusidic acid or a pharmaceutically acceptable salt or solvate thereof but does not need to occur over the entire treatment period. In another embodiment, the treatment regimen includes pretreatment with one agent, followed by the addition of the other agent or agents. Alternating sequences of administration are also contemplated. Alternating administration includes administration of fusidic acid or a pharmaceutically acceptable salt or solvate thereof, followed by the additional agent, followed by fusidic acid or a pharmaceutically acceptable salt or solvate thereof, etc. The aforementioned sequences can also be administered in several cycles wherein each cycle may be similar or different with each possibility representing a separate embodiment. The therapeutic efficacy of the combination of fusidic acid or a pharmaceutically acceptable salt or solvate thereof and the additional agent(s) is at least additive. In some embodiments, the therapeutic efficacy is synergistic, namely the overall dose of each of the components may be lower, thus resulting in significantly lower side effects experienced by the subject, while a sufficient desirable therapeutic effect is nonetheless achieved. When combination therapy is involved, fusidic acid or a pharmaceutically acceptable salt or solvate thereof and the additional therapeutic agent(s) may be provided in a single dosage form such as a fixed-dose combination or in separate compositions intended for simultaneous administration.

As used herein and in the appended claims, the singular forms "a", "an", and "the" include plural references unless the context clearly dictates otherwise. It should be noted that the term "and" or the term "or" are generally employed in its sense including "and/or" unless the context clearly dictates otherwise.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1

In vitro testing for the susceptibility of *H. pylori* to sodium fusidate was performed. Inoculation was made with a broth culture of two ATCC strains of *H. pylori* (ATCC No. 700824 and 43826) diluted to match a 0.5 McFarland turbidity standard. Disks containing increasing antibiotic concentrations (0.5-4.0%) were placed on seeded bacterial lawn on agar surface. Three disks with the same antibiotic concentration were placed on each plate. The disks were evenly distributed in a circle towards the periphery of the plate. Plates were incubated for 4 days at an incubation temperature of 37° C. (with Microaerophilic pach). Diameter of inhibition sizes was measured wherein each disk was considered to represent the center of the clear zone, namely the slope of the regression line is construed to correspond to the diffusion coefficient of the antibiotic in the agar. Negative control disks containing water instead of antibiotics were placed at the center of each dish. A separate plate with no disks was prepared as an additional control. The plate showed bacterial growth of both ATCC strains. The results are outlined in Table 1 below:

TABLE 1

| | Diameter of inhibition [cm] | | | | | |
|---|---|---|---|---|---|---|
| | *H. pylori* strains | | | | | |
| | ATCC No. 700824 | | | ATCC No. 43826 | | |
| | Sodium fusidate con. (%) | | | | | |
| Sample No. | 0.5 | 1.0 | 4.0 | 0.5 | 1.0 | 4.0 |
| 1 | 2 | 2.6 | ≥4.4 | ≥4.4 | ≥4.4 | ≥4.4 |
| 2 | 2.4 | 3.0 | ≥4.4 | ≥4.4 | ≥4.4 | ≥4.4 |
| 3 | 1.6 | 2.7 | ≥4.4 | ≥4.4 | ≥4.4 | ≥4.4 |
| Negative Control | 0 | 0 | NT | ND | ND | NT |

NT—Not Tested
ND—Not detectable due to a full antibiotic inhibition caused by the diffusion of the antibiotics from the disks at the periphery of the plate to its center.

Example 2

Agar dilution is used to determine *H. pylori* antimicrobial susceptibility to fusidic acid or sodium fusidate or a combination of fusidic acid or sodium fusidate with other antibiotics. Agar dilution antimicrobial susceptibility is performed according to the National Committee for Clinical Laboratory Standards (NCCLS) Approved standard M7-A5: Methods for dilution antimicrobial susceptibility tests for bacteria that grow aerobically 5$^{th}$ Ed., 2000.

1. Agar plates

Muller-Hinton Agar (MHA) medium is prepared according to manufacturer's instructions. After gelling, the agar's pH at room temperature is determined. A pH range between 7.2 and 7.4 is acceptable. 5% aged sheep blood (≥2 weeks old) is added to the MHA. Immediately after autoclaving, the agar is cooled down to 45-50° C. in a water bath before aseptically adding anti-microbial solutions and heat-labile supplements, and pouring the plates. When antibiotic other than fusidic acid or sodium fusidate is tested, the following substances may be added to the MHA: NaCl, oxacillin, nafcillin, methicillin, and glucose-6-phosphate.

2. Dilution plates

Fusidic acid or sodium fusidate is incorporated into a Muller-Hinton Agar (MHA) medium, with each plate containing a different concentration. A drug free test is used as control. Intermediate (10×) antimicrobial agent solutions are prepared by performing successive two-fold dilutions (1:2, 1:4, and 1:8). Then, one part of the 10× antimicrobial solution is added to nine parts of molten agar.

3. Inoculum preparation

*H. pylori* strain ATCC 43504 is used. Commercially available McFarland standard 4 (108 CFU/ml) from latex particles is used for the inoculum. McFarland standard 4 is mixed by gently inverting the latex particles (not on a vortex mixer) immediately before use.

4. Inoculating agar dilution plates

*H. pylori* are transfected by applying it to the agar surface by an inoculum replicator.

5. Incubation

The inoculated plates are allowed to stand at room temperature until the moisture in the inoculum spots has been absorbed into the agar, i.e., until the spots are dry, but no more than 30 minutes. The plates are incubated at 37±1° C. for 72 hours.

6. Determination of agar dilution end points

The plates are placed on a dark, nonreflecting surface to determine the end points. The Minimum Inhibitory Concentration (MIC) is determined as the lowest concentration of antimicrobial agent that completely inhibits growth, disregarding a single colony or a faint haze caused by the inoculum. MIC is compared with conventional antibiotics against *H. pylori*.

Example 3

Different doses of fusidic acid or sodium fusidate are prepared by dilution of stock solutions. 1.0 mL of each dose is added to test tubes (typically 16×125 mm or 18×150 mm). 9.0 mL of *H. pylori* ATCC 43504 McFarland 4 standard is added to each test tube followed by incubation at 36° C.-37.5° C. for 72 hours. After incubation, 0.5 mL of dilute formaldehyde is added to each tube. The concentration of *H.*

*pylori* is determined using a spectrophotometer by comparing to reference dilutions of a standard.

Example 4

Colonies from a 2-3 day culture are suspended on a blood agar plate in sterile distilled water. The density is adjusted to equal a McFarland 3 standard. A swab dipped in the suspension is used to inoculate evenly the entire surface of the plate. The medium is typically Mueller-Hinton agar or Wilkins-Chalgren agar with 5-10% horse blood. The plate is allowed to dry and Etest strip is applied followed by incubation at 35° C. in microaerophilic conditions for 3-5 days. The MX of fusidic acid or sodium fusidate is read at the point of complete inhibition of all growth, including hazes and isolated colonies.

Example 5

*H. pylori* is hosted for experimental purposes in mice, piglets, monkeys, cats, gerbils, guinea pigs, ferrets, and beagle dogs. Infection assessment and efficacy of treatment with fusidic acid or sodium fusidate is determined by urease map, IgG, lesions and/or histology using protocols detailed in Gastroenterology, 1990, 99(2): 352-361; Gastroenterology, 1994, 106: 1405-1417; Infect. Immun., 1987, 55: 2789-2796; and Infect. Immun., 1990, 58: 2606-2612.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

The invention claimed is:

1. A method for treating *Helicobacter* infection or suppressing *Helicobacter* replication in a subject in need thereof, the method comprising
the step of administering to the subject a pharmaceutical composition consisting of
(a) a therapeutically effective amount of fusidic acid or a pharmaceutically acceptable salt or solvate thereof, wherein the therapeutically effective amount ranges from 0.001 to 1,000 mg per kg body weight of the subject; and
(b) the remainder of the pharmaceutical composition by weight contains
(i) at least one pharmaceutically acceptable excipient; and
(iii) optionally, another drug selected from the group consisting of
a proton pump inhibitor,
a $H_2$ receptor antagonist,
an antacid,
an antibiotic other than fusidic acid or a pharmaceutically acceptable salt or solvate thereof, and
a combination thereof.

2. The method of claim 1, wherein the *Helicobacter* species is *Helicobacter pylori*.

3. The method of claim 1, wherein the pharmaceutical composition is suitable for oral administration in the form selected from the group consisting of tablet, pill, capsule, pellets, granules, powder, lozenge, sachet, cachet, elixir, suspension, dispersion, emulsion, solution, syrup, aerosol, ointment, and suppository.

4. The method of claim 1, wherein the fusidic acid or a pharmaceutically acceptable salt or solvate thereof is administered at a daily dose.

5. The method of claim 1, wherein the fusidic acid or a pharmaceutically acceptable salt or solvate thereof has a minimum inhibitory concentration (MIC) of about 10 μg/ml or less against *Helicobacter*.

6. The method of claim 1, wherein
(a) the proton pump inhibitor is selected from the group consisting of omeprazole, lansoprazole, pantoprazole, rabeprazole, tenatoprazole and pharmaceutically acceptable salts thereof;
(b) the antibiotic is selected from the group consisting of metronidazole, clarithromycin, amoxicillin, tetracycline, doxycycline, levofloxacin, rifabutin, and rifamycin;
(c) the $H_2$ receptor antagonist is selected from the group consisting of cimetidine, ranitidine, famotidine, roxatidine, nizatidine, and lafutidine;
(d) the antacid is selected from the group consisting of aluminum hydroxide, magnesium hydroxide, sodium bicarbonate, potassium bicarbonate, magnesium carbonate, calcium carbonate, aluminum silicate, magnesium silicate, aminoacetic acid, magnesium metasilicic aluminate, magnesium oxide, bismuth citrate, bismuth subcitrate, bismuth salicylate, bismuth subsalicylate, bismuth tartrate, bismuth sodium tartrate, bismuth nitrate, bismuth gallate, and bismuth subgallate; and
(e) the pharmaceutically acceptable excipient is selected from the group consisting of a binder, a filler, a surfactant, an anti-tacking agent, a plasticizer, a lubricant, a glidant, a disintegrant, a diluent, a tonicity enhancing agent, a wetting agent, a buffering substance, a colorant, a preservative, and any combination thereof.

7. The method of claim 1, wherein co-administration of the therapeutic agents is performed in a regimen selected from a single combined composition.

8. A method for treating a gastric or duodenal ulcer associated with *Helicobacter* infection in a subject in need thereof, the method comprising the step of administering to the subject a pharmaceutical composition comprising a therapeutically effective amount of fusidic acid or a pharmaceutically acceptable salt or solvate thereof.

9. The method of claim 8, wherein the *Helicobacter* species is *Helicobacter pylori*.

10. The method of claim 8, wherein the pharmaceutical composition is suitable for oral administration in the form selected from the group consisting of tablet, pill, capsule, pellets, granules, powder, lozenge, sachet, cachet, elixir, suspension, dispersion, emulsion, solution, syrup, aerosol, ointment, and suppository.

11. The method of claim 8 wherein the fusidic acid or a pharmaceutically acceptable salt or solvate thereof is administered at a daily dose of about 0.001 to about 1,000 mg per kg body weight.

12. The method of claim 8, wherein the fusidic acid or a pharmaceutically acceptable salt or solvate thereof have a minimum inhibitory concentration (MIC) of about 10 μg/ml or less against *Helicobacter*.

13. The method of claim 8, wherein the pharmaceutical composition is co-administered in combination with at least one other drug.

14. The method of claim 13, wherein the at least one other drug comprises a proton pump inhibitor, a $H_2$ receptor antagonist, an antacid, an antibiotic other than fusidic acid or a pharmaceutically acceptable salt or solvate thereof, or a combination thereof.

15. The method of claim 14, wherein the proton pump inhibitor comprises at least one of omeprazole, lansoprazole, pantoprazole, rabeprazole, tenatoprazole and pharmaceutically acceptable salts thereof; or wherein the antibiotic comprises at least one of metronidazole, clarithromycin, amoxicillin, tetracycline, doxycycline, levofloxacin, rifabutin, and rifamycin; or wherein the $H_2$ receptor antagonist comprises at least one of cimetidine, ranitidine, famotidine, roxatidine, nizatidine, and lafutidine; or wherein the antacid comprises at least one of aluminum hydroxide, magnesium hydroxide, sodium bicarbonate, potassium bicarbonate, magnesium carbonate, calcium carbonate, aluminum silicate, magnesium silicate, aminoacetic acid, magnesium metasilicic aluminate, magnesium oxide, bismuth citrate, bismuth subcitrate, bismuth salicylate, bismuth subsalicylate, bismuth tartrate, bismuth sodium tartrate, bismuth nitrate, bismuth gallate, and bismuth subgallate.

16. The method of claim 13, wherein co-administration of the therapeutic agents is performed in a regimen selected from a single combined composition, separate individual compositions administered substantially at the same time, and separate individual compositions administered under separate schedules.

\* \* \* \* \*